United States Patent [19]

Wendel et al.

[11] Patent Number: 4,687,766
[45] Date of Patent: Aug. 18, 1987

[54] PHARMACEUTICAL PREPARATION FOR THE THERAPEUTIC TREATMENT OF RHEUMATIC DISEASES

[75] Inventors: Armin Wendel, Cologne; Sigurd Leyck, Pulheim; Helmut Wetzig, Pulheim-Sinnersdorf; Jorg Hager, Cologne; Manfred Durr, Pulheim-Dansweiler; Miklos Ghyczy, Cologne, all of Fed. Rep. of Germany

[73] Assignee: A. Natterman & Cie, GmbH, Cologne, Fed. Rep. of Germany

[21] Appl. No.: 685,152

[22] Filed: Dec. 21, 1984

[51] Int. Cl.$^4$ .................... A61K 31/655; A61K 31/54
[52] U.S. Cl. ..................... 514/78; 514/222; 514/825
[58] Field of Search ........... 514/78, 222, 825

[56] References Cited

U.S. PATENT DOCUMENTS

| 4,309,421 | 1/1982 | Ghyczy et al. | 514/78 |
| 4,425,276 | 1/1984 | Günther | 260/403 |
| 4,443,378 | 4/1984 | Günther | 260/403 |
| 4,452,743 | 6/1984 | Günther | 260/403 |

FOREIGN PATENT DOCUMENTS 2039738 8/1980 United Kingdom ................. 514/78

OTHER PUBLICATIONS

Merck Index, 9th ed., pp. 711 & 712, No. 5287, 1976.

Primary Examiner—Johnnie R. Brown
Assistant Examiner—John W. Rollins
Attorney, Agent, or Firm—Burns, Doane, Swecker & Mathis

[57] ABSTRACT

Pharmaceutical preparation containing phospholipids for the therapeutic treatment of rheumatic diseases which contain in addition to the antiphlogistically acting oxicam derivatives of the general formula

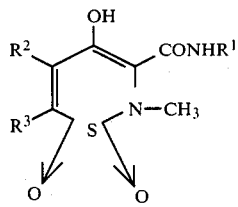

special 1,2-diacyl-glycero-3-phosphocholines wherein 75–86% by weight of the acyl radicals are unsaturated fatty acid radicals, and the preparation thereof.

16 Claims, No Drawings

PHARMACEUTICAL PREPARATION FOR THE THERAPEUTIC TREATMENT OF RHEUMATIC DISEASES

BACKGROUND OF THE INVENTION

The object of the present invention is a new pharmaceutical preparation containing phospholipids for the therapeutic treatment of rheumatic diseases.

A large number of nonsteroidal antirheumatics are used in the treatment of rheumatic diseases. One of the most frequently applied groups of substances are the oxicams, such as for example piroxicam. Rheumatism therapy is usually long term. Medicines, the therapeutic application whereof as a rule is necessary over an extended period of time, must satisfy specific requirements in relation to their therapeutic breadth. As a consequence of the daily intake of such medicines, high stresses on the gastrointestinal tract as the absorption location, on the liver as the preferred bioconversion organ, and the elimination tracts, are unavoidable.

It is known that in the course of extended treatments with oxicams for example gastrointestinal disorders, including hemorrhaging, hemotopesis, disorders, headaches, vertigo, damage to the liver and kidneys, and edemas may occur. The most frequent side effects are gastrointestinal disturbances. Oxicams are metabolized or eliminated through the liver and the kidneys. This, however, may lead in particular in the case of patients with restricted liver or renal functions to considerable side effects. In patients with preexisting liver function disorders increased caution is required as the reduced bioconversion increases the danger of possible side effects. Thus, for example it was necessary to withdraw sudoxicam (4-hydroxy-2-methyl-N-(2-thiazolyl)2H-1,2-benzthiazine-3-carboxyamide-1,1-dioxide) from clinical testing because of considerable liver toxicity (Side Effects of Drugs, Annual 6; Excerpta Medica 1982, p. 103). DE-PS No. 28 56 333 discloses an improvement of the gastointestinal tolerance of nonsteroidal antiphlogistics by the addition of phospholipids, wherein the molar ratio of the active ingredient to the phospholipid may amount to up to 1:20.

It is the object of the present invention to provide a pharmaceutical preparation for the treatment of rheumatic diseases containing as the specific active ingredient oxicam derivatives and exhibiting increased tolerance in particular with respect to the liver, without altering the inflammation inhibiting effect of the oxicams.

SUMMARY OF THE INVENTION

The present invention is a pharmaceutical preparation for the therapeutical treatment of rheumatic diseases. The pharmaceutical preparation contains phospholipids and nonsteroidal antiphlogistic agents in a molar ratio of 1:1 to 20:1. The antiphlogistic agents are present in an inflammation inhibiting effective amount and are oxicam derivatives of the formula

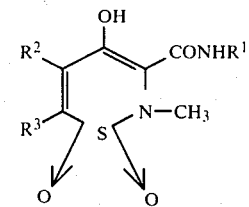

wherein $R^1$ represents a heterocyclic ring, such as for example pyridine or 5-methyl-3-isoxazole and $R^2$ together with $R^3$ an aromatic ring condensed on, such as for example the benzene or thiophene ring. The phospholipids are present in an effective gastric inflammation alleviating amount and are specific 1,2-diacyl-glycero-3-phosphocholines wherein 75–86% by weight of the acyl radicals are unsaturated fatty acid radicals or their mixture, with a chain length of 16, 18 and/or 20 carbon atoms.

DETAILED DESCRIPTION OF THE INVENTION

It has been found in an entirely surprising manner that in the case of low doses of oxicam derivatives the improvement in the tolerance by the gastrointestinal tract of oxicam derivatives described in DE-PS No. 28 56 333 by their combination with phospholipids is not always obtained, but is valid for high doses only. If, however, the oxicam derivatives are combined with specific 1,2-diacylglycero-3-phosphocholines, defined as 1,2-diacylglycero-3-phosphocholines wherein the acyl represents mainly unsaturated fatty acid radicals with 16, 18 and/or 20 carbon atoms, the effect desired is obtained not only in the gastrointestinal tract, but the tolerance of the product is improved in the liver also. The specific 1,2-diacyl-glycero-3-phosphocholines comprise 75–86% by weight of unsaturated fatty acid radicals. 1,2-diacyl-glycero-3-phosphocholines are preferred; they contain as the fatty acid radicals linolic acid and/or linolenic acid and/or oleic acid and/or arachidonic acid radicals or fatty acid radical mixtures of the following composition:

10–20% by weight palmitic acid
3–5% by weight stearic acid
8–12% by weight oleic acid
62–69.5% by weight linolic acid
4–7% by weight linolenic acid, wherein the individual contents in the acyl residues are chosen so that they total 100% by weight, and the proportion of unsaturated acyl radicals is at least 75% and at the most 86% by weight with respect to the total amount of acyl radicals.

The following is an example wherein the limiting values total 100% by weight and the upper and lower limits of the unsaturated acyl radicals are attained:

20–10% by weight palmitic acid
5–4% by weight stearic acid
10–12% by weight oleic acid
62–68% by weight linolic acid
3–6% by weight linolenic acid.

Especially preferred are the 1,2-diacylglycero-3-phosphocholines, wherein the 1- and 2-acyl radicals represents different fatty acid radical mixtures.

In these preferred 1,2-diacyl-glycero-3-phosphocholines the acyl radical in the 1-position consists of the following fatty acid radical mixtures:

22–26% by weight palmitic acid
6–9% by weight stearic acid
8–12% by weight oleic acid
50–54% by weight linolic acid
4–6% by weight linolenic acid
and the acyl radical in the 2-position consists of the following mixtures of fatty acid radicals:
1–2% by weight palmitic acid
0–1% by weight stearic acid
8–12% by weight oleic acid
78–85% by weight linolic acid
5–8% by weight linolenic acid.
wherein the individual contents of the acyl radicals are chosen so that a total of 100% by weight is obtained and the proportion of unsaturated acyl residues is at least 75% by weight and at the most 86% by weight.

The following is an example wherein the limiting values add up to 100% by weight in this manner:
1-acyl radical:
22–26% by weight palmitic acid
7–9% by weight stearic acid
12–9% by weight oleic acid
54–50% by weight linolic acid
5–6% by weight linolenic acid
2-acyl radical:
1–3% by weight palmitic acid
0–2% by weight stearic acid
8–12% by weight oleic acid
85–75% by weight linolic acid
6–8% by weight linolenic acid The specific 1,2-diacyl-glycero-3-phosphocholines correspond to the following general formula:

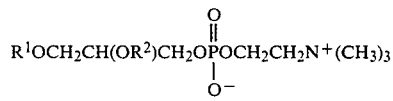

wherein $R^1$ and $R^2$ may be identical or different and the radicals $$CH_3(CH_2)_l(CH{:}CHCH_2)_m(CH_2)_nCO-$$

wherein
$l = 1, 4, 7, 8$ or $10$
$m = 0, 1, 2, 3$ or $4$
$n = 2$ or $6$
represent for example the following radicals:

$$CH_3(CH_2)_{14}CO-$$

$$CH_3(CH_2)_{16}CO-$$

$$CH_3(CH_2)_7CH{:}CHCH_2(CH_2)_6CO-$$

$$CH_3(CH_2)_4(CH{:}CHCH_2)_2(CH_2)_6CO-$$

$$CH_3CH_2(CH{:}CHCH_2)_3(CH_2)_6CO-$$

$$CH_3(CH_2)_4(CH{:}CHCH_2)_4(CH_2)_2CO-$$

The specific 1,2-diacyl-glycero-3-phosphocholines may contain optionally up to 20% by weight of additional 1,2-diacyl-glycero-3-phosphates or their mixtures, such as for example 1,2-diacyl-glycero-3-phosphoethanolamine, 1,2-diacyl-glycero-3-phosphoinositol, 1,2-diacyl-glycero-3-phosphoserine, 1,2-diacylglycero-3-phosphoglycerol, but in particular 1,2-diacyl-glycerol-3-phosphoethanolamine. These additional phosphocholines comprise as the acyl radicals the same fatty acid radical mixtures as the specific 1,2-diacyl-glycero-3-phosphocholines. The special 1,2-diacyl-glycerol-3-phosphocholines may be obtained by known processes (EP No. 54 770, EP No. 54 768, EP No. 54 769) in particular from soybeans.

Compounds of the following General Formula I may be employed as the oxicam derivatives:

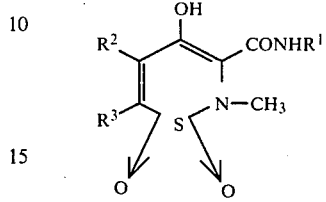

wherein $R^1$ signifies a heterocyclic ring, such as for example pyridine or 5-methyl-3-isoxazole, and $R^2$ together with $R^3$ an aromatic ring condensed onto it, such as for example the benzene or thiophene ring.

Examples of the compounds of Formula I are:
4-hydroxy-2-methyl-N-(2-pyridyl)-2H-1,2-benzothiazine-3-carboxamide-1,1-dioxide (piroxicam),
4-hydroxy-2-methyl-N-(5-methyl-3-isoxazolyl) 2H-1,2-benzo-thiazine-3-carboxamide-1,1-dioxide (isoxicam),
4-hydroxy-2-methyl-N-(2-pyridyl)-2H-thieno [2,3-e]-1,2-thiazine-3-carboxamide-1,1-dioxide (tenoxicam), and
4-hydroxy-2-methyl-N-(2-thiazolyl)-2H-1,2-benzothiazine-3-carboxamide-1,1-dioxide (sudoxicam).

The oxicams may be combined with the special 1,2-diacyl-glycero-3-phosphocholines in a molar ratio of 1:1 to 1:20, preferably in a molar ratio of 1:1 to 1:10. A unit dose for the therapeutic application to humans amounts to 5–300 mg oxicam combined with 10–500 mg 1,2-diacyl-glycerol-3-phosphocholine per day, preferably 10–20 mg for piroxicam and 100–300 mg for isoxicam combined with 50–250 mg 1,1-diacyl-glycero-3-phosphocholine.

The special 1,2-diacyl-glycero-3-phosphocholines, as shown by whole animal autoradiographs, are accumulated rapidly and permanently in the stomach and intestine mucosa and particularly in the liver, after oral administration and form a durable protection against damage by drugs. As shown by in vivo experiments on rats, the negative enzyme changes induced in the liver by antiphlogistic agents may be normalized by the addition of the special 1,2-diacyl-glycero-3-phosphocholines.

For the administration or use of the new combination of special 1,2-diacyl-glycero-3-phosphocholines and oxicams the combination is converted into a suitable form, such as for example capsules, solutions, emulsions, tablets, powder or chewable capsules.

The special 1,2-diacyl-glycero-3-phosphocholines may be filled in combination with the oxicams by a known process into soft gelatine capsules or more advantageously into hard gelatine capsules, for example by the process described in DE-OS No. 30 22 136, optionally with the aid of suitable auxiliary and filler substances. The soft or hard gelatine capsules may be swallowed whole or they may be chewed.

To produce the hard gelatine chewing capsules the special 1,2-diacyl-glycero-3-phosphocholines are mixed, together with the oxicams, with pharmaceutically inert carrier substances, such as for example waxes, hydrated oils, natural, semisynthetic or synthetic triglycerides and their mixtures, such as cocoa butter, and conventional suppository masses, for example based on triglycerides, such as for example Witepsol suppository masses (H. P. Fiedler, Lexikon der Hilstoffe for Pharmazie, Kosmetid und angrenzende Gebiete [Encyclopedia of auxiliary substances for the pharmaceutical, cosmetic and related fields], 1971, Vol. 9 p. 548–50 and 632–634); fatty alcohols; solid hydrocarbons, such as vaseline or solid paraffin; saturated fatty acids, such as lauric acid, myristic acid, palmitic acid, stearic acid; emulsifiers, such as ethoxylated triglycerides, polyethoxylated vegetable oils; fatty acid sugar esters; silicones, gelatine, methylcellulose; hydroxypropoxycellulose; hydroxypropylcellulose; polyethylene glycols; polyvinylpyrrolidone; polyvinylalcohol, polyacrylic acid and their salts.

Ethanol is added to the masses in an amount such that a concentrated product but one that is flowable at room temperature or slightly elevated temperatures, is obtained, i.e. that the product at such a temperature has just the lowered or not lowered viscosity for transportation and that this product may be filled in known filling installations with an auxiliary installation for liquid filling and with a heatable filler nozzle, similar to the methods described in DE-OS No. 30 22 136.

The special 1,2-diacyl-glycero-3-phosphocholines may be processed together with the oxicams by the process wherein they are worked for example into the viscous 1,2-diacyl-glycero-3-phosphocholine masses prior to the filling, or added after the filling of the 1,2-diacyl-glycero-3-phosphocholines in a powder or tablet form. To produce tablets and powder mixtures the special 1,2-diacyl-glycero-3-phosphocholines are converted into a solid form. Because of the viscosity of the substances, this is extremely difficult. However, by the addition of 2–10% by weight of calcium chloride, solid preparations are obtained.

To produce solid preparations, the special 1,2-diacyl-glycero-3-phosphocholines are dissolved or emulsified with the addition of the usual auxiliary substances in water or an organic solvent, for example alcohols, such as methanol, ethanol or isopropanol, in hydrocarbons, such as hexane, chlorinated hydrocarbons or their mixtures, the calcium chloride added, the mixture agitated with slight heating and subsequently the solvent drawn off. A dry powder is obtained.

Calcium chloride is added in amounts of 1–20%, in particular 2–10%, with respect to the weight of 1,2-diacyl-glycero-3-phosphocholine.

Preferred solvents for the 1,2-diacyl-glycero-phosphocholines are alcohols, in particular ethanol. Wash liquids are water or alcohols, such as methanol or ethanol. Conventional methods, such as vacuum roll drying, spray drying, freeze drying, are suitable for drying. The dried, comminuted 1,2-diacyl-glycero-3-phosphocholine-calcium chloride mixtures may also be comminuted or granulated by the usual processes. To stabilize the products, advantageously 0.1–2% by weight with respect to the 1,2-diacyl-glycero-3-phosphocholine used of a stabilizer or stabilizer mixture, such as tocopherol acetate and/or ascorbic acid palmitate, is added.

The production of the solid, oral forms of the drug, consisting of oxicams and the special 1,2-diacyl-glycero-3-phosphocholines may also be effected by the following process:

Powder mixtures:

The oxicams and a 1,2-diacyl-glycero-3-phosphocholine-calcium chloride mixture comminuted to the proper grain size, are mixed together with the addition of conventional galenic auxiliary substances and pressed into tablets or filled into capsules.

Spray deposition:

The solution or dispersion of the oxicam in organic solvents or water are mixed together with a solution or emulsion of the 1,2-diacyl-glycero-3-phosphocholine in organic solvents or water and the solution of calcium chloride in water or organic solvents, optionally with further conventional galenic auxiliary substances, and spray dried. The spray dried product obtained may be pressed with the addition of further galenic auxiliary substances into tablets or filled into capsules.

Coated products:

The solution or emulsion of the special 1,2-diacyl-glycero-3-phosphocholines in organic solvents or water are mixed with a solution of the calcium chloride in organic solvents or water and applied in a fluid bed to the oxicam previously comminuted to the grain sized desired. The powdered, free flowing product is either pressed into tablets with the addition of galenic auxiliary materials or filled into capsules. The ratio of the oxicam to the 1,2-diacyl-glycero-3-phosphocholine/calcium chloride may vary as a function of the therapeutic requirements within molar ratios of 1:0.5 to 1:20. Advantageously, depending on the dosage of the oxicam, 50–250 mg of the 1,2-diacyl-glycero-3-phosphocholine-calcium chloride mixture are added.

The specific 1,2-diacyl-glycero-3-phosphocholines used in the following examples comprise in the two positions acyl radicals of the aforedescribed mixtures.

In order to further illustrate the present invention and the advantages thereof, the following specific examples are given, it being understood that these examples are intended only to be illustrative without serving as a limitation on the scope of the present invention.

EXAMPLE 1 a. Oxicam powder mixture

Piroxicam: 100 g

Tablettose (special aluminumhydroxysilicate): 800 g

Avicel (microcrystalline cellulose): 60 g

Aerosil (pyrogenic silica): 20 g

Sodium carboxymethyl starch: 10 g

Magnesium stearate: 10 g

The substances are mixed homogeneously.

b. Filler mass

Special 1,2-diacyl-glycero-3-phosphocholine: 9 kg

Polyethylene glycol 400: 1 kg

Ethanol: 0.3 kg are mixed homogeneously in a kneader at 60° C.

c. Of the filler mass described under b. in a hard gelatine capsule machine with the addition for liquid filling 160 mg of the mixture are measured out per hard gelatine capsule of size 2. Subsequently, in the same hard gelatine capsule filling machine with the aid of a filler station for powder, 100 mg of the powder mixture described under a. are added and the capsule sealed.

The capsules contain 50 to 250 mg 1,2-diacyl-glycero-3-phosphocholine and 10–20 mg nonsteroidal antiphlogistic agents.

EXAMPLE 2 a. Oxicam powder mixture

Piroxicam: 100 g

Tablettose (special aluminumhydroxysilicate): 800 g

Avicel (microcrystalline cellulose): 60 g

Aerosil (pyrogenic silica): 20 g

Sodium carboxymethyl starch: 10 g
Magnesium stearate: 10 g
The substances are mixed homogeneously and pressed into 100 mg tablets with a diameter of 5 mm.
  b. Filler mass
Special 1,2-diacyl-glycero-3-phosphocholine: 76.5 kg
Witepsol suppository mass: 14.3 kg
Soybean oil: 9.2 kg
Ethanol: 3.0 kg
are mixed homogeneously in a kneader at 60° C.
  c. In a hard gelatine capsule machine with a filler station for liquid 270 mg of the filler mass described under b. are filled into a hard gelatine capsule of size 2. Subsequently, in the same machine with the aid of a filler station for tablets a pressed tablet of the composition described under a. is inserted into the capsule and the capsule sealed.

EXAMPLE 3

Piroxicam: 100.0 g
Special 1,2-diacyl-glycero-3-phosphocholine: 76.5 g
Witepsol suppository mass: 14.3 g
Soybean oil: 9.2 g
Ethanol: 3.0 g
are mixed in a storage vessel and heated with agitation to approx. 40° C. The solution is filled in a capsule filling installation of the Zanasi AZ 20L type by the metering device, which is heated to 80° C., into capsules at a rate of 12,000 capsules per hour. The mixture immediately solidifies in the capsule. The capsule may be sealed and taken from the installation.

EXAMPLE 4

Piroxicam capsules:
Piroxicam: 10.0 mg
Silica: 3.7 mg
Special 1,2-diacyl-glycero-3-phosphocholine: 50.0 mg
Calcium chloride: 1.3 mg
  250 g special 1,2-diacyl-glycero-phosphocholine are dissolved in 400 ml chloroform and mixed with a solution of 6.875 g calcium chloride, anhydrous, in 70 ml methanol. This solution is sprayed in a fluid bed onto a powder mixture of 50 g piroxicams, ground to less then 50 $\mu$m and 18.5 g silica. The granules obtained are screened to over 0.5 mm and filled into hard gelatine capsules with 10 mg piroxicam.

EXAMPLE 5

Isoxicam capsules:
Isoxicam: 100.0 mg
Silica: 5.1 mg
Special 1,2-diacyl-glycero-3-phosphocholine: 100.0 mg
Calcium chloride: 6.9 mg
Preparation as in Example 4.

EXAMPLE 6

Tenoxicam capsules:
Tenoxicam: 10.0 mg
Silica: 3.5 mg
Special 1,2-diacyl-glycero-3-phosphocholine: 50.0 mg
Calcium chloride: 1.5 mg
Preparation as in Example 4.

EXAMPLE 7

Piroxicam tablets:
Piroxicam: 10.0 mg
Special 1,2-diacyl-glycero-3-phosphocholine: 50.0 mg
Silica: 10.0 mg
Calcium chloride: 4.0 mg
Sodium carboxymethyl starch: 10.0 mg
Microcrystalline cellulose: 26.0 mg
Magnesium stearate: 10.0 mg
  500 g special 1,2-diacyl-glycero-3-phosphocholine are dissolved in 1000 ml chloroform, mixed with 40 g calcium chloride, anhydrous, in 500 ml methanol and sprayed in a fluid bed onto a powder mixture containing 100 g piroxicam ground to less then 50 $\mu$m, and 10 g silica. The product obtained is mixed with 90 g silica, 100 g sodium carboxymethyl starch, 260 g microcrystalline cellulose and 100 g magnesium stearate in a conventional powder mixer and pressed into tablets with 10 mg piroxicam.

EXAMPLE 8

Piroxicam capsules:
Piroxicam: 20 mg
Special 1,2-diacyl-glycero-3-phosphocholine: 100 mg
Silica: 40 mg
Microcrystalline cellulose: 40 mg
  500 g special 1,2-diacyl-glycero-3-phosphocholine, comminuted, are ground cold with the addition of 150 g silica. The powder obtained is mixed after reaching room temperature with 50 g silica and 200 g calcium hydrogen phosphate and filled into capsules at 20 mg piroxicam.

The pharmaceutical preparations prepared according to the examples are used for the treatment of rheumatic diseases and exhibit substantially lesser side effects compared with active oxicam ingredients administered in identical doses with respect to inflammations of the gastrointestinal tract and damage to the liver.

RESEARCH REPORT ON THE EFFECTIVENESS OF THE COMBINATION OF THE INVENTION

1. Acute test

Male rats with a weight of approximately 160 g were used in the experiments. The experimental animals receive a diet of soft rolls for 3 days, which is discontinued one day before the onset of the experiments. Tap water remains available ad libitum.

The control and treated groups consist of 10 animals each. The substances are administered p. o. in a volume of 5 ml/kg body weight. Three and a half hours after the administration of the substance the stomachs are removed and examined for ulcers. Evaluation is performed macroscopically with the aid of index numbers. The ulcer frequently is determined additionally. Reference: K. Takagi, S. Okabe: Jap. J. Pharmacol., Vol. 18, 1968, 9–18.

2. Subacute test

Male rats, fed in a normal manner, with a weight of approx. 160 g are used in the experiment. The control and treated groups consist of 10 animals each.

The animals receive the test substance on three successive days, p. o., in a volume of 5 ml/kg body weight. Three and a half hours after the last application of the substance the stomachs are removed and examined and evaluated as in the acute test.

Acute Test

| Oxicam (number of animals) | mg/kg | Ulcer index Oxicam alone | Ulcer index Oxicam + phospholipid[2] (1:2 molar) | Change in the ulcer index in % |
|---|---|---|---|---|
| Piroxicam (n = 30) | 10.0 | 1.1 | 0.5 | −55 |
|  | 31.6 | 1.5 | 0.7 | −53 |
|  | 56.2 | 2.7 | 0.6 | −78 |
| Sudoxicam (n = 10) | 10.0 | 0.8 | 0.4 | −50 |
|  | 31.6 | 1.2 | 0.6 | −50 |
|  | 100.0 | 1.5 | 0.7 | −53 |
| Piroxicam[1] (n = 10) | 10.0 | 2.8 | 1.0 | −64 |
|  | 17.8 | 3.1 | 2.2 | −29 |
|  | 31.6 | 3.3 | 2.0 | −39 |

[1]Animals received a normal diet prior to fasting for 24 hours
[2]Phospholipid = 1,2-diacyl-glycero-3-phosphocholine, in which approximately 75% by weight of the acyl radical represent unsaturated fatty acid radicals.

Subacute Test

| Oxicam (number of animals) | mg/kg | Ulcer index Oxicam alone | Ulcer index Oxicam + phospholipid[1] (1:2 molar) | Change in the ulcer index in % |
|---|---|---|---|---|
| Piroxicam (n = 10) | 10.0 | 0.9 | 0.5 | −44 |
|  | 31.6 | 1.0 | 0.5 | −50 |
|  | 56.2 | 1.2 | 0.3 | −75 |

[1]Phospholipid: 1,2-diacyl-glycero-3-phosphocholine, in which 75% by weight of the acyl radicals represent unsaturated fatty acid radicals.

Comparison of the effectiveness of phosphatidylcholine exclusively with saturated fatty acid residues as the acyl groups and the special phospatidylcholine to be used according to the invention with mainly unsaturated fatty acid radicals The conditions of the aforedescribed acute and subacute test are applied.

Acute Test

| Oxicam (number of animals) | Dose mg/kg | Ulcer index Oxicam alone | Ulcer index Oxicam + phospholipid[1] (1:2 molar) | Ulcer index Oxicam + phospholipid[2] (1:2 molar) | Change in the ulcer index in % |
|---|---|---|---|---|---|
| Piroxicam (n = 30) | 10.0 | 1.1 | 0.5 | — | −55 |
|  | 31.6 | 1.5 | 0.7 | — | −53 |
|  | 56.2 | 2.7 | 0.6 | — | −78 |
| Piroxicam (n = 10) | 10.0 | 1.2 | — | 1.3 | +8 |
|  | 31.6 | 1.9 | — | 2.0 | +5 |
|  | 56.2 | 2.1 | — | 1.2 | −30 |

[1]Phospholipid: 1,2-diacyl-glycero-3-phosphocholine, in which approx. 75% by weight of the acyl radicals represent unsaturated fatty acids
[2]Phospholipid: 1,2-diacyl-glycero-3-phosphocholine, in which the acyl radicals represent saturated fatty acids.

The tabular presentation of the experimental results shows that in the case of low doses of piroxicam as the active ingredient the desired effect in the gastrointestinal tract does not occur with phospholipids containing exclusively saturated fatty acid radicals.

The comparative experiment was continued with piroxicam and dichlofenac and indomethacin in an acute test (10 animals each).

| Compound | Dose mg/kg | Active ingredient alone | Ulcer index saturated fatty acids as acyl radicals phospholipid:ingredient (2:1) (molar) | Change of index % |
|---|---|---|---|---|
| Piroxicam | 10 | 1.2 | 1.3 | +8 |
|  | 31.6 | 1.9 | 2.0 | +5 |
|  | 56.2 | 2.1 | 1.2 | −30 |
| Diclofenac | 31.6 | 1.4 | 0.7 | −50 |
|  | 100 | 2.5 | 1.7 | −32 |
|  | 316 | 3.4 | 1.7 | −50 |
| Indomethacin | 5.62 | 0.7 | 0.4 | −43 |
|  | 10 | 1.1 | 0.7 | −36 |
|  | 17.8 | 1.6 | 0.7 | −56 |

This comparison shows that in the case of other active ingredients the desired effect is obtained with phospholipids with saturated fatty acid radicals even with lower doses, but in the case of piroxicam with higher doses only. The comparative experiment shows that for the oxicam derivatives special conditions must be present and special phospholipids must be chosen to obtain the desired effect with low doses.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A pharmaceutical preparation for the treatment of rheumatic diseases, containing a phospholipid and a nonsteroidal antiphlogistic agent in a molar ratio of 1:1 to 20:1, comprising
    (a) an inflammation inhibiting effective amount of an oxicam derivative which is piroxicam, isoxicam, tenoxicam or sudoxicam, and
    (b) an effective gastric inflammation inhibiting amount of a 1,2-diacyl-glycero-3-phosphocholine wherein 75–86% by weight of the acyl radicals are unsaturated fatty acid radicals with a chain length of 16, 18 or 20 carbon atoms or their mixture.

2. A pharmaceutical preparation according to claim 1, wherein piroxicam is the oxicam derivative.

3. A pharmaceutical preparation according to claim 1, wherein isoxicam is the oxicam derivative.

4. A pharmaceutical preparation according to claim 1, wherein tenoxicam is the oxicam derivative.

5. A pharmaceutical preparation according to claim 1, wherein the unsaturated fatty acid radicals of the 1,2-diacylglycero-3-phosphocholine are linolic acid, oleic acid, linolenic acid or arachidonic acid radicals.

6. A pharmaceutical preparation according to claim 5, wherein it contains in addition to the 1,2-diacyl-glycero-3-phosphocholine up to 20% of a 1,2-diacyl-glycero-3-phosphate, wherein the acyl radicals are unsaturated fatty acid radicals with a chain length of 16, 18 or 20 carbon atoms or their mixture.

7. A pharmaceutical preparation according to claim 6, wherein the 1,2-diacyl-glycero-3-phosphate is 1,2-diacyl-glycero-phosphoethanolamine, 1,2-diacyl-glycero-3-phosphoinositol, 1,2-diacyl-glycero-3-phosphoserine, or 1,2-diacyl-glycero-3-phosphoglycerol.

8. A pharmaceutical preparation according to claim 1, wherein the acyl radicals are a mixture of fatty acid radicals of:
    10–20% by weight palmitic acid,
    3–5% by weight stearic acid, 8–12% by weight oleic acid,
62–69.5% by weight linolic acid, and
4–7% by weight linolenic acid;
and wherein the acyl radical contents are chosen so that they total 100%, and the proportion of unsaturated acyl radicals is at least 75% by weight and at the most 86% by weight with respect to th total amount of the acyl radicals.

9. A pharmaceutical preparation according to claim 1, wherein the 1- acyl radical contains:
22–26% by weight palmitic acid,
6–9% by weight stearic acid,
8–12% by weight oleic acid,
50–54% by weight linolic acid, and
4–6% by weight linolenic acid;
and the 2- acyl radical contains:
1–2% by weight palmitic acid,
0–1% by weight stearic acid,
8–12% by weight oleic acid,
75–85% by weight linolic acid, and
5–8% by weight linolenic acid,
as the mixture of fatty acid radicals; and wherein the acyl radical contents in the 1- and 2-positions each total 100% by weight and the proportion of unsaturated acyl radicals is at least 75% by weight and at the most 86% by weight.

10. A pharmaceutical preparation according to claim 6, wherein it contains per unit dose 10–20 mg piroxicam and 50–250 mg 1,2-diacyl-glycero-3-phosphocholine.

11. A pharmaceutical preparation according to claim 1, wherein it contains per unit dose 5–20 mg of an oxicam derivative and 10–500 mg 1,2-diacylglycero-3-phosphocholine, in addition to auxiliary and filler substances.

12. A process for the production of a pharmaceutical preparation according to claim 1, wherein the oxicam derivative is stirred in the presence of an auxiliary substance into a liquid mass of a 1,2-diacyl-glycero-3-phosphocholine and subsequently filled in the liquid form into a hard gelatin capsule.

13. A process for the production of a pharmaceutical preparation according to claim 1, wherein the oxicam derivative and the 1,2-diacyl-glycero-3-phosphocholine aere dissolved or emulsified together in water or an organic solvent, 1–20% by weight of calcium chloride which has been dissolved or slurried in water or an alcohol is added, the solvent drawn off, and the product obtained dried.

14. A process for the production of a pharmaceutical preparation according to claim 1, wherein the oxicam derivative is comminuted to the grain size desired and mixed together with a powdered, 1,2-diacylglycero-3-phosphocholine-calcium chloride mixture containing 1–20% by weight of calcium chloride.

15. A process for the production of a pharmaceutical preparation according to claim 1, wherein the solution or dispersion of the oxicam derivative in an organic solvent or water is mixed with a solution or emulsion of the 1,2-diacyl-glycero-3-phosphocholine in an organic solvent or water and a solution of 1–20% by weight of calcium chloride in an organic solvent or water and spray dried, and the spray dried product obtained is pressed into a tablet or filled into a capsule.

16. A process for the production of a pharmaceutical preparation according to claim 1, wherein a solution of emulsion of the 1,2-diacyl-glycero-3-phosphocholine in an organic solvent or water is mixed with a solution of 1–20% by weight of calcium chloride in an organic solvent or water and applied in a fluid bed to the oxicam previously comminuted to the grain size desired; the powdered, free flowing product obtained is pressed with the addition of galenic auxiliary substances into a tablet or filled into a capsule.

* * * * *